United States Patent [19]

Jost

[11] Plant 5,211

[45] Mar. 27, 1984

[54] NECTARINE TREE, "SUMMER RED"

[76] Inventor: Donald J. Jost, 9633 S. Rio Vista Ave., Reedley, Calif. 93654

[21] Appl. No.: 446,851

[22] Filed: Dec. 3, 1982

[51] Int. Cl.[3] ..... A01H 5/03

[52] U.S. Cl. ..... Plt./41

[58] Field of Search ..... Plt./41

*Primary Examiner*—Robert E. Bagwill

*Attorney, Agent, or Firm*—Huebner & Worrell

[57] ABSTRACT

A nectarine tree bearing yellow-fleshed clingstone fruit of large size which ripens a minimum of four days before the fruit of the Flamekist (an unpatented variety developed by the U.S. Department of Agriculture) and which has skin having an extensive red skin coloration, typically 60 to 90 percent, and having a very waxy and bright finish.

1 Drawing Figure

BACKGROUND OF THE NEW VARIETY

The present invention relates to a new and distinct variety of nectarine tree bearing fruit which ripens a minimum of four days before fruit of the Flamekist variety (an unpatented variety of nectarine tree developed by the U.S. Department of Agriculture) of which the new variety is a sport. The new variety bears yellow-fleshed, clingstone fruit which is of large and uniform size and of uniform shape and which has a skin particularly distinguished from that of the Flamekist variety by having a substantially more complete red coloration and by having a brighter, more waxy finish. The new variety has been named "Summer Red" for commercial marketing.

A factor contributing favorably to the sale of fresh nectarines is a large extent of red skin coloration. The qualities of the Flamekist variety of nectarine tree have gained it substantial commercial success since its introduction in 1968, even though its fruits develop at best partial red skin coloration. A new varity of nectarine tree bearing fruit generally similar to those of the Flamekist variety but having a more extensive red coloration is, therefore, even more advantageous, especially if the appearance of fruit of the new variety are further enhanced by a very bright, waxy finish. Another factor contributing to the desirability of a variety of fruit tree is the availability of its fruit in the fresh market at a time when similar fruit are not available, so that the fruit of such variety commands a higher price. As a result, a new variety of nectarine tree bearing fruit having, in general, the desirable qualities of fruit of the Flamekist variety is particularly desirable since the fruit of the new variety matures somewhat earlier than those of the Flamekist variety.

ORIGIN AND ASEXUAL REPRODUCTION OF THE NEW VARIETY

The subject variety of nectarine tree was discovered by me in August 1975, as a mutation involving a single scaffold limb of a Flamekist nectarine tree (an unpatented variety developed by the U.S. Department of Agriculture) in a bearing, commercial orchard of such trees owned by me and located at 9633 South Rio Vista Avenue near the City of Reedley, in the County of Fresno, in the State of California. The mutation was asexually reproduced under my supervision on property owned by me at said location by budding onto 20 peach trees of the Nemaguard (unpatented) variety of August 1980, and tree and fruit characteristics resulting from such budding as observed in 1982 proved identical to those of the original mutation.

SUMMARY OF THE NEW VARIETY

The subject variety of nectarine tree bears clingstone, yellow-fleshed fruit of large and uniform size and of uniform shape. The subject variety is particularly characterized by its fruit attaining full commercial maturity a minimum of four days prior to fruit of the Flamekist variety and in having a more extensive red skin coloration. When grown at the above-designated location near Reedley, Calif., a location in which the Flamekist variety, typically, attains a 15 to 20 percent red skin coloration and sometimes retains a fully yellow skin coloration, the subject variety at such maturity, typically, develops a 60 to 90 percent red coloration, and develops at least a 40 percent red coloration. The suture of the new variety is inconspicuous, the suture coloration blending into the general skin coloration. The fruit of the subject variety is further characterized by its skin having an attractive, very bright and waxy finish.

BRIEF DESCRIPTION OF THE DRAWING

The accompanying drawing is a color photograph of mature nectarines of the subject variety together with a typical twig bearing characteristic leaves, one of the nectarines being divided substantially at the suture plane to show the flesh and stone characteristics.

DETAILED DESCRIPTION

Referring more particularly to the pomological details of the new and distinct variety of nectarine tree, the following have been observed under the ecological conditions prevailing at the above-identified location near Reedley, Fresno County, Calif., in August 1982 with the fruit of the new variety at full commercial maturity. All of the color plate designations are by reference to the Maerz and Paul *Dictionary of Color*, Second Edition, 1950, common descriptive color names also being used.

TREE

Size: Large.

Vigor: Vigorous.

Form: Moderately upright when young, spreading with age and crop, modified by pruning.

Bearing: Regular and productive.

Trunk: Medium thickness, medium surface texture; older bark greyish-brown (16-C-5) with numerous lenticels.

Branches: Medium in size and surface texture. Mature one year old shoots brownish in color (15-E-7). Young shoots green (19-J-4).

Leaves:

*Size.*—Medium; average measurements at midpoint of vigorous shoots: length 18 cm, width 4.4 cm.

*Form.*—Lanceolate with tip acuminate, often slightly twisted and curved to one side.

*Color.*—Upper leaf surface green (23-L-8), lower leaf surface lighter green (22-H-7).

*Leaf margin.*—Crenate, tipped with small brownish gland (15-E-12); margin gently undulate; leaf blade slightly recurved downwardly.

*Petiole.*—Medium size, average 11 mm long, 1 to 1.5 mm thick, light greenish-yellow (18-H-3) in color.

*Stem glands.*—Number 3 to 4; most often all glands on one basal area of leaf blade, occasionally 1 to 2 glands on petiole; medium size; reniform; greenish (18-H-4) when young.

*Stipules.*—Usually two at base of petiole, 8 to 10 mm long; light green (18-I-4) in color; early deciduous.

FRUIT

Maturity: In 1982, first pick August 12; full commercial maturity August 14; last pick August 16.

Size: Uniform; large: average axial diameter 67 mm; average suture diameter 65 mm; average cheek diameter 67 mm.

Form: Uniform; nearly globose in axial aspect; broadly ovate in lateral aspect; symmetrical to slightly uneven.

*Suture.*—A shallow line extending from base to apex, slightly deeper over basal shoulder to base and 15 to 25 mm along apical shoulder to apex; suture line discontinuous at apex but visible beyond apex on dorsal suture side 7 to 12 mm with a marked depression; suture inconspicuous with color blending well into general fruit color; suture shows no light yellow color band sometimes apparent in other high-color sports; suture usually visible also on dorsal side of base, from base to dorsal shoulder.

*Ventral surface.*—Generally rounded; only slightly lipped, usually toward apex end; and usually slightly stronger on one side.

*Stem cavity.*—Oval in axial aspect; medium depth, 8 to 10 mm; width 12 to 15 mm; length 19 to 22 mm.

*Base.*—Generally rounded and at right angle to fruit axis.

*Apex.*—Very short and usually rounded, although slightly variable; pistil point apical and at times depressed.

Stem: Medium length, average 10 to 12 mm; average thickness 3 mm; color, yellow green (20-K-1).

Skin: Thick; medium texture; no obvious tendency to crack; skin relatively free of acidity when fully mature; tenacious to flesh; blush color red (4-L-5) to dark red (6-L-5) covering 40 to 90 percent of fruit surface; ground color bright yellow (10-K-1) on unblushed surfaces; pubescence, lacking; finish very waxy, bright and attractive; lenticels inconspicuous with almost no dots or speckling on surface.

Flesh: Light yellow (10-K-2) in color with no red coloration extending in from skin or in flesh except 1 to 3 mm from pit cavity; surface of pit cavity dark red (7-L-5) with white fibers.

Ripening: Evenly.

Texture: Firm, meaty, crisp, softens slowly becoming moderately juicy.

Fibers: Moderate in number, fine, tender.

Aroma: Slight, pleasant.

Flavor: Good, mild, slightly acid until fully ripe.

Stone: Clingstone; adheres to flesh over most of stone surface.

*Size.*—Medium: average length 40 mm, average width 27 mm; average thickness 20 mm.

*Form.*—Obovate in lateral aspect, slightly truncated at base.

*Base.*—Very slightly oblique to stone axis toward ventral suture; somewhat more necked and raised than average along margin of hilum.

*Hilum.*—Moderately broad, oval.

*Apex.*—Rounded, tip cuspidate and sharp.

*Sides.*—Nearly equal.

*Ridges.*—Numerous over axial shoulder in lateral aspect and generally parallel to apex edge down to mid-stone; stone deeply grooved near apex with tops of ridges relatively smooth; some short grooves over basal shoulder converging basally.

*Pits.*—Circular to oval, generally smooth in outline.

*Ventral edge.*—Thick with coalesced short wings converging apically; edge moderately prominent near base.

*Dorsal edge.*—Moderately full with relatively shallow, tight groove extending base to apex; apical shoulder only slightly eroded, occasionally nearly smooth.

*Color.*—Brownish-gray (15-A-6); variable, often tinged with purple-red (55-L-7).

*Tendency to split.*—Slight.

Use: Fresh market for local and long-distance shipping.

Keeping quality: Good.

Shipping quality: Good.

Resistance to insects and disease: No particular susceptibilities noted.

Although the new variety of nectarine tree possesses the described characteristics as a result of growing conditions in Fresno County, Calif., in the central part of the San Joaquin Valley, it is to be understood that variations of the usual magnitude in characteristics incident to growing conditions, fertilization, pruning and pest control are to be expected.

Having thus described and illustrated my new variety of nectarine tree, I claim:

1. A new and distinct variety of nectarine tree which bears generally yellow-fleshed, clingstone fruit of large and uniform size and characterized as to novelty by bearing fruit which ripens a minimum of four days before the Flamekist variety of nectarine tree, an unpatented variety developed by the U.S. Department of Agriculture, and by a skin which has at full maturity a waxy and bright finish and extensive red coloration, typically spreading over from 60 to 90 percent of its surface area, with the suture coloration blending into the general skin coloration.

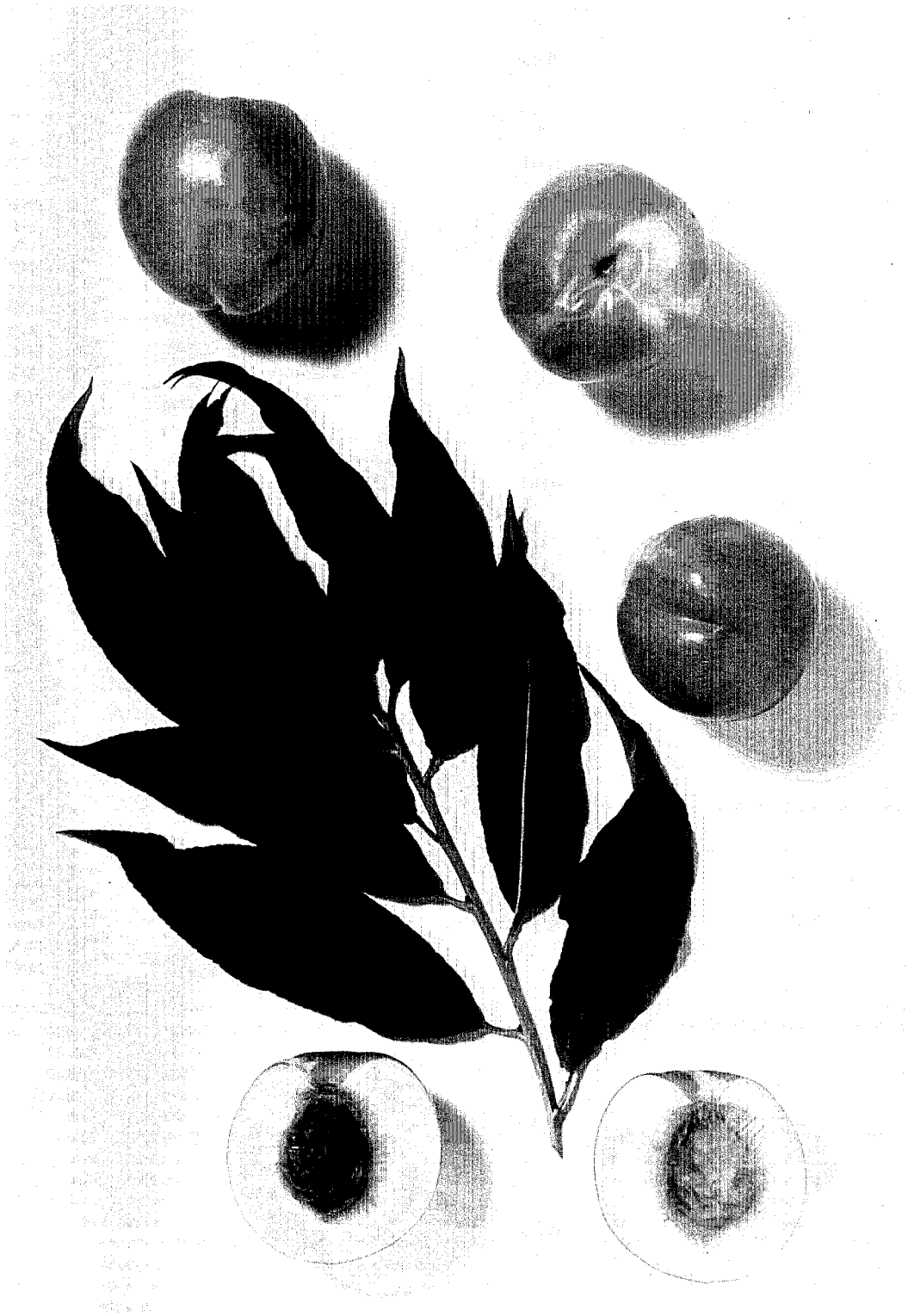

* * * * *